(12) United States Patent
Zou et al.

(10) Patent No.: US 11,874,023 B2
(45) Date of Patent: Jan. 16, 2024

(54) HUMIDIFIER

(71) Applicant: Shenzhen Jingxintai Houseware Co., Ltd., Shenzhen (CN)

(72) Inventors: Jinshan Zou, Shenzhen (CN); Shouyong Zheng, Shenzhen (CN); Bo Fan, Shenzhen (CN)

(73) Assignee: SHENZHEN JINGXINTAI HOUSEWARE CO., LTD., Shenzhen (CN)

( * ) Notice: Subject to any disclaimer, the term of this patent is extended or adjusted under 35 U.S.C. 154(b) by 114 days.

(21) Appl. No.: 17/525,952

(22) Filed: Nov. 14, 2021

(65) Prior Publication Data

US 2022/0074612 A1 Mar. 10, 2022

Related U.S. Application Data

(63) Continuation-in-part of application No. PCT/CN2019/090568, filed on Jun. 10, 2019.

(30) Foreign Application Priority Data

May 29, 2019 (CN) .......................... 201910457088.2

(51) Int. Cl.
*F24F 6/12* (2006.01)
*F24F 11/89* (2018.01)
(Continued)

(52) U.S. Cl.
CPC ...... *F24F 6/12* (2013.01); *A61L 9/14* (2013.01); *F24F 8/50* (2021.01); *F24F 11/89* (2018.01);
(Continued)

(58) Field of Classification Search
CPC ...... F24F 6/12; F24F 8/50; F24F 11/89; F24F 2006/008; A61L 9/14; A61L 2209/134; A61L 2209/11; A61L 2209/132
See application file for complete search history.

(56) References Cited

U.S. PATENT DOCUMENTS

| 857,111 A | * | 6/1907 | Rice, Jr. | F02M 19/035 |
| | | | | 123/142.5 R |
| 1,111,763 A | * | 9/1914 | Rogers | F02M 19/035 |
| | | | | 48/189.5 |

(Continued)

FOREIGN PATENT DOCUMENTS

| CN | 102798187 A | 11/2012 |
| CN | 204345773 U | 5/2015 |

(Continued)

OTHER PUBLICATIONS

EPO translation of CN207831563 (Year: 2018).*

*Primary Examiner* — Stephen Hobson
(74) *Attorney, Agent, or Firm* — MATTHIAS SCHOLL P.C.; Matthias Scholl

(57) ABSTRACT

A humidifier includes a first housing, a second housing, a water atomization module, an essential oil delivery module, and an essential oil container. The first housing includes an outer wall including a recess. The second housing is fixedly embedded in an upper part of the recess. The water atomization module is disposed in the first housing. The water atomization module includes a first container, a water passage, and an ultrasonic atomizer. The water flows out of the first container, enters the water passage into the ultrasonic atomizer, and is atomized to produce mist. The essential oil delivery module is disposed in the second housing. The essential oil container is connected to the essential oil delivery module. The essential oil delivery module is configured to transfer essential oil from the essential oil container to the water passage so that the essential oil and the water are atomized together.

7 Claims, 6 Drawing Sheets

(51) Int. Cl.
*F24F 8/50* (2021.01)
*A61L 9/14* (2006.01)
*F24F 6/00* (2006.01)

(52) U.S. Cl.
CPC ... *A61L 2209/134* (2013.01); *F24F 2006/008* (2013.01)

(56) References Cited

U.S. PATENT DOCUMENTS

| | | | | |
|---|---|---|---|---|
| 4,595,564 A * | 6/1986 | Spector | B05B 7/1686 | 422/4 |
| 4,752,422 A * | 6/1988 | Uchida | B05B 17/0615 | 261/DIG. 85 |
| 6,196,527 B1 * | 3/2001 | Huang | F24F 6/18 | 261/DIG. 85 |
| 6,378,845 B1 * | 4/2002 | Hsu | F24F 6/00 | 239/289 |
| 7,984,832 B2 * | 7/2011 | Pivonka | A45D 34/04 | 222/321.9 |
| 8,544,826 B2 * | 10/2013 | Ediger | F24F 6/12 | 261/78.2 |
| 8,827,247 B2 * | 9/2014 | Kanel | F24F 6/02 | 261/81 |
| 9,022,365 B2 * | 5/2015 | Brosmith | A61L 9/122 | 261/142 |
| 9,278,365 B2 * | 3/2016 | Banco | A01M 1/2055 | |
| 9,358,557 B2 * | 6/2016 | Young | A61L 9/14 | |
| 9,511,166 B1 * | 12/2016 | Li | B05B 7/2416 | |
| 10,894,268 B2 * | 1/2021 | Ou | B05B 17/0607 | |
| 11,197,941 B1 * | 12/2021 | Gao | B05B 7/0012 | |
| 11,213,600 B2 * | 1/2022 | Hsiao | A61L 9/037 | |
| 11,590,520 B2 * | 2/2023 | Seeberger | B05B 15/50 | |
| 2004/0067181 A1 * | 4/2004 | Shin | A61L 9/22 | 422/123 |
| 2007/0217771 A1 * | 9/2007 | Granger | A01M 1/2033 | 392/386 |
| 2007/0284765 A1 * | 12/2007 | Wang | F24F 11/0008 | 261/DIG. 85 |
| 2008/0193339 A1 * | 8/2008 | Pankhurst | A61L 9/035 | 422/123 |
| 2009/0122516 A1 * | 5/2009 | Yang | A61L 9/122 | 362/96 |
| 2010/0084484 A1 * | 4/2010 | Sevy | A61M 11/001 | 239/340 |
| 2012/0154760 A1 * | 6/2012 | Nutter | F24F 6/00 | 353/57 |
| 2013/0175362 A1 * | 7/2013 | Lee | F24F 6/14 | 239/302 |
| 2013/0334336 A1 * | 12/2013 | Haran | A61L 9/14 | 239/102.1 |
| 2015/0174595 A1 * | 6/2015 | Young | A61L 9/14 | 261/78.2 |
| 2017/0065998 A1 * | 3/2017 | Tun | A45D 20/122 | |
| 2017/0153040 A1 * | 6/2017 | Wang | F24F 13/28 | |
| 2017/0224864 A1 * | 8/2017 | Le | A61L 9/14 | |
| 2019/0041075 A1 * | 2/2019 | Sarkar | F24F 11/62 | |
| 2020/0096210 A1 * | 3/2020 | Kim | F24F 13/28 | |
| 2020/0114114 A1 * | 4/2020 | Harrington | A61M 16/161 | |
| 2022/0072183 A1 * | 3/2022 | Zou | B05B 7/2491 | |
| 2022/0074612 A1 * | 3/2022 | Zou | F24F 8/50 | |
| 2022/0305167 A1 * | 9/2022 | Wei | A61L 9/013 | |
| 2023/0116964 A1 * | 4/2023 | Sun | F24F 11/63 | 700/276 |

FOREIGN PATENT DOCUMENTS

| | | | |
|---|---|---|---|
| CN | 108534279 | A | 9/2018 |
| CN | 207831563 | * | 9/2018 |
| CN | 207831563 | U | 9/2018 |
| CN | 110081544 | A | 8/2019 |
| JP | 2010002155 | A | 1/2010 |

* cited by examiner

HUMIDIFIER

CROSS-REFERENCE TO RELATED APPLICATIONS

This application is a continuation-in-part of International Patent Application No. PCT/CN2019/090568 with an international filing date of Jun. 10, 2019, designating the United States, now pending, and further claims foreign priority benefits to Chinese Patent Application No. 201910457088.2 filed May 29, 2019. The contents of all of the aforementioned applications, including any intervening amendments thereto, are incorporated herein by reference.

BACKGROUND

The disclosure relates to a humidifier for atomization of water and essential oil.

Conventionally, essential oil diffusers and humidifiers are two kinds of independent products. That is, conventional essential oil diffusers do not have humidification function, and the humidifiers do not have aroma-diffusing function.

SUMMARY

The disclosure provides a humidifier comprising a first housing, a second housing, a water atomization module, an essential oil delivery module, and an essential oil container; the first housing comprises an outer wall comprising a recess; the recess corresponds to the second housing in shape; the second housing is fixedly embedded in an upper part of the recess; the water atomization module is disposed in the first housing; the water atomization module comprises a first container, a water passage, and an ultrasonic atomizer; the water flows out of the first container, enters the water passage into the ultrasonic atomizer, and is atomized to produce mist; the essential oil delivery module is disposed in the second housing; the essential oil container is connected to the essential oil delivery module; the essential oil delivery module is configured to transfer essential oil from the essential oil container to the water passage so that the essential oil and the water can be atomized together.

In a class of this embodiment, the essential oil delivery module comprises a head, an essential oil tube, a fixing member, and a peristaltic pump; the head is connected to the essential oil container; the essential oil tube is disposed through the head into the essential oil container; the essential oil tube comprises an essential oil discharge section and the fixing member is configured to fix the essential oil discharge section; the peristaltic pump is configured to expel the air out of the essential oil tube so that the essential oil moves in the essential oil tube.

In a class of this embodiment, the second housing comprises a bottom wall comprising a through hole; the head is disposed on the bottom wall of the second housing; the essential oil container is disposed through the through hole to connect to the head; the peristaltic pump is fixedly disposed in the second housing and above the head; the essential oil tube comprises a flexible tube; one end of the essential oil tube is disposed through the head into the essential oil container; the other end of the essential oil tube is fixed in the first housing by the fixing member; the peristaltic pump comprises a rotating part; a middle part of the essential oil tube is disposed through the rotating part; and the flexible tube is clamped or released as the rotating part rotates.

In a class of this embodiment, the fixing member comprises a hollow channel, and at least part of the essential oil tube is disposed in the hollow channel; the humidifier further comprises a sidewall shared by the first housing and the second housing; the sidewall comprises a mounting hole; the fixing member further comprises an arc-shaped end disposed through the mounting hole and extending into the first housing; the essential oil flows out of the arc-shaped end and drips into a set position of the first housing.

In a class of this embodiment, the first housing comprises a side wall, a partition, and a bottom plate; the partition is disposed above the bottom plate; the partition is connected to the side wall to form a first space for accommodation of the first container; and a second space is defined by the bottom plate, the partition, and the side wall.

In a class of this embodiment, the water passage is disposed below the partition and is configured to store the water flowing out of the first container; the water passage comprises an atomization part disposed on a central axis (i.e. a middle or central part) of the first housing; the water flows through the atomization part and is atomized to produce mist.

In a class of this embodiment, the ultrasonic atomizer is disposed in the second space; the water in the water passage flows through the atomization part and is atomized by the ultrasonic atomizer to produce the mist.

In a class of this embodiment, the first container is a hollow cylinder comprising a bottom surface and a side surface; the hollow cylinder further comprises an overflow channel and an open top communicating with the overflow channel; the overflow channel is disposed along a central axis of the hollow cylinder, is disposed through the bottom surface and communicates with the water passage; the overflow channel is configured to allow the mist from the ultrasonic atomizer to flow out of the humidifier; the overflow channel comprises a lateral surface and is in the shape of a cylinder, a cone, or a truncated cone; a water container is defined by the bottom surface, the side surface, and the lateral surface and is configured to store the water; and a vertical projection of the overflow channel on the bottom surface is coincident with the atomization part.

In a class of this embodiment, the first container further comprises a water outlet disposed on the bottom surface and is configured to allow the water to flow from the first container to the water passage; the water outlet is disposed above the water passage; the humidifier further comprises a water flow control module disposed at the water outlet; the water flow control module is mechanically or electrically controlled to allow the water to flow from the first container to the water passage.

In a class of this embodiment, the humidifier further comprises a third housing and a control unit is disposed in the third housing; the control unit is configured to control a working time and/or working state of the water atomization module and the essential oil delivery module; and the third housing is embedded in a lower part of the recess.

The following advantages are associated with the humidifier of the disclosure: the water atomization module is used in conjunction with the essential oil delivery module to disperse a controlled amount of the essential oil in the water. In this way, the humidifier has the dual function of atomization of water and essential oil. The control unit is configured to control the working time of the essential oil delivery module so as to independently control the amount of the essential oil dripped onto the water passage. Such a humidifier offers advantages such as simple operation and low cost.

Figure 1:
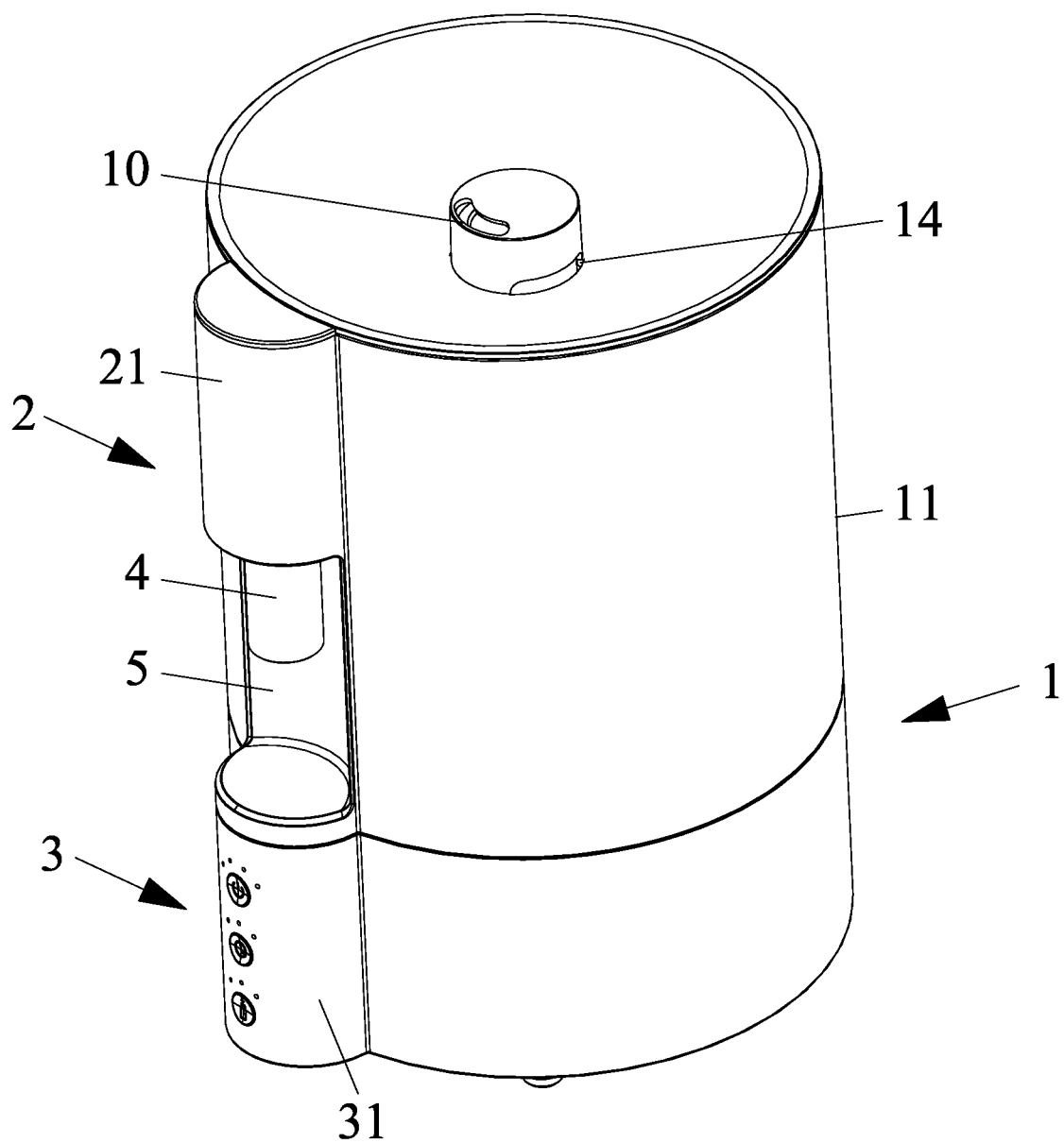
FIG. 1 is a perspective view of a humidifier according to one embodiment of the disclosure.

In the drawings, the following reference numbers are used: 1. Water atomization module; 2. Essential oil delivery module; 3. Control unit; 4. Essential oil container; 5. Recess; 10. Opening; 11. First housing; 12. First container; 14. Overflow channel; 15. Water passage; 16. Ultrasonic atomizer; 17. Atomization part; 18. Bottom plate; 19. Partition; 21. Second housing; 22. Head; 23. Peristaltic pump; 24. Fixing member; 25. Essential oil tube; 31. Third housing; 141. Lateral surface; 142. Filter; 151. Arc-shaped part; and 152. Water outlet.

DETAILED DESCRIPTION

To further illustrate the disclosure, embodiments detailing a humidifier are described below. It should be noted that the following embodiments are intended to describe and not to limit the disclosure.

Figure 2:
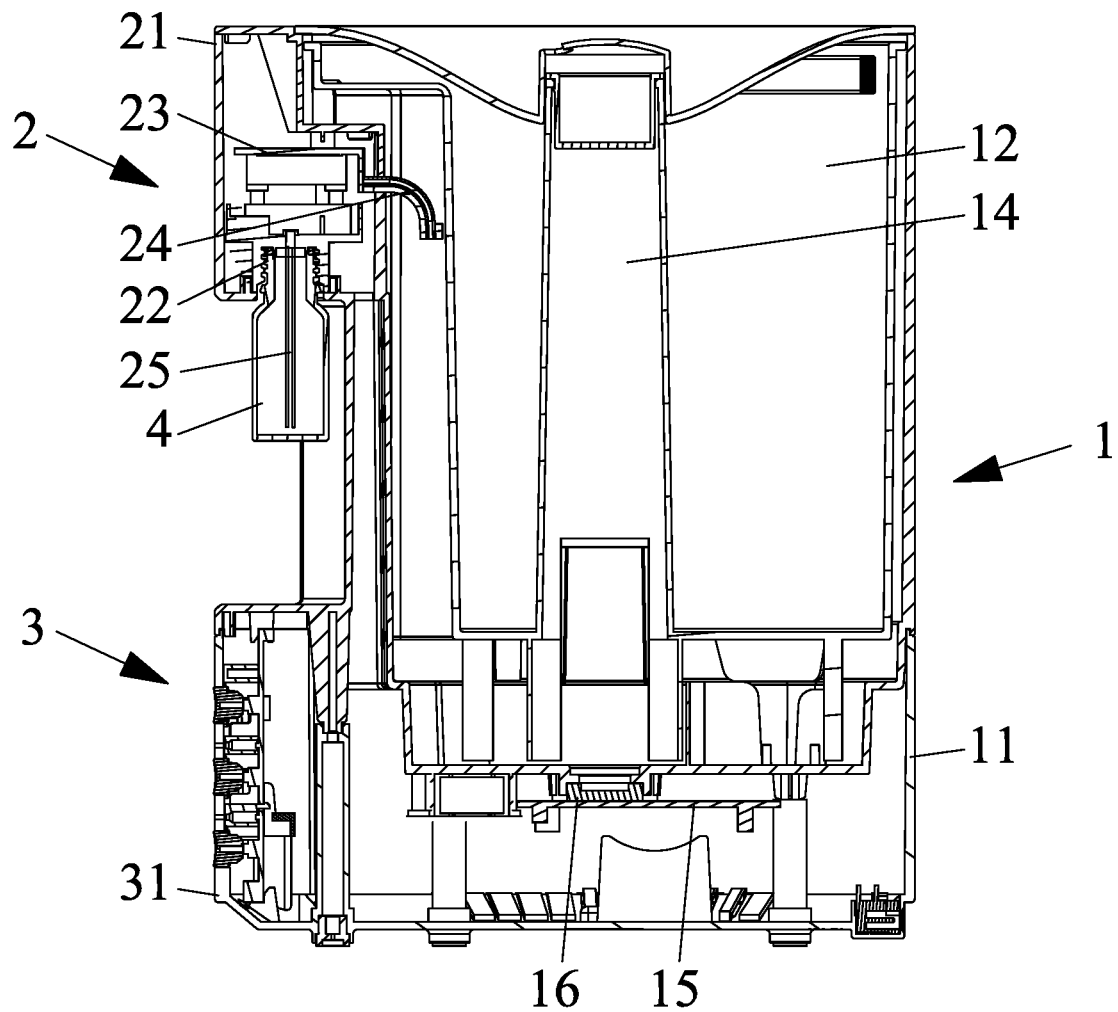
FIG. 2 is a cross-sectional view of a humidifier according to one embodiment of the disclosure.

Referring to FIGS. 1 and 2, a humidifier comprises a first housing 11, a water atomization module 1, a second housing 21, an essential oil delivery module 2, a control unit 3, and an essential oil container 4. The water atomization module 1 is disposed in the first housing 11. The essential oil delivery module 2 is disposed in the second housing 21. The essential oil container 4 is connected to the essential oil delivery module 2. The water atomization module 1 comprises a first container 12, a water passage 15, and an ultrasonic atomizer 16. The ultrasonic atomizer 16 is configured to atomize the water flowing out of the first container 12, that is, the water flows out of the first container 12, enters the water passage 15 into the ultrasonic atomizer 16, and is atomized to produce mist. The first container 12 and parts for water atomization such as the water passage 15 and the ultrasonic atomizer are all disposed in the first housing 11. The essential oil delivery module 2 is configured to transfer the essential oil from the essential oil container 4 to the water passage 15 so that the essential oil and the water can be atomized together to produce vapor. Referring to FIG. 1, the first housing 11 comprises an opening 10. The vapor flows outs of the opening 10 to increase moisture levels in the air. In the example, the essential oil delivery module 2 is fixedly disposed in the second housing 21. The first housing 11 comprises an outer wall comprising a recess 5. The recess 5 corresponds to the second housing 21 in shape. The second housing 21 is fixedly embedded in an upper part of the recess 5 as shown in FIG. 2.

The essential oil delivery module 2 comprises a head 22, an essential oil tube 25, a fixing member 24, and a peristaltic pump 23. The head 22 is connected to the essential oil container 4. The essential oil tube 25 is inserted through the head 22 into the essential oil container 4. The essential oil tube 25 comprises an essential oil discharge section and the fixing member 24 is configured to fix the essential oil discharge section. The peristaltic pump 23 is configured to expel the air out of the essential oil tube 25 so that the essential oil moves in the essential oil tube 25. The second housing 21 comprises a bottom wall comprising a through hole. The head 22 is disposed on the bottom wall of the second housing 21. The essential oil container 4 is disposed through the through hole to connect to the head 22. The peristaltic pump 23 is fixedly disposed in the second housing and above the head 25. The essential oil tube 25 comprises a flexible tube. One end of the essential oil tube is disposed through the head 22 into the essential oil container 4. The other end of the essential oil tube 25 is fixed in the first housing 11 by the fixing member 24. The peristaltic pump 23 comprises a rotating part. A middle part of the essential oil tube 25 is disposed through the rotating part. The flexible tube is clamped or released as the rotating part rotates. In the example, the essential oil tube 25 is a continuous flexible tube through which the essential oil is transferred from the essential oil container 4 to the first housing 12. In certain examples, the essential oil tube 25 comprises a plurality of segments with a specific length. The plurality of segments is connected together to form a channel that passes through the peristaltic pump 23. In the example, the working time of the peristaltic pump 23 is a key to regulate the amount of the essential oil per unit time supplied to the first housing 11 for atomization, thus controlling the concentration of the essential oil in the mist.

In the example, the head 22 comprises a female thread. The essential oil container 4 comprises a top opening comprising a male thread. The male thread is screwed to the female thread so that the head 22 is fixedly connected to the essential oil container 4, thus preventing leakage of the essential oil and increasing use efficiency of the essential oil.

In the example, the control unit 3 is configured to control the peristaltic pump 23, which allows for the timely and quantitative transportation of the essential oil from the essential oil container 4 to the water atomization module 1. The essential oil is dispersed in the water and atomized to humidify the air and produce a fragrant scent. The essential oil container 4 and the first container 12 are independent of each other so that the supplement of the water and the essential oil cannot effect each other.

Figure 3:
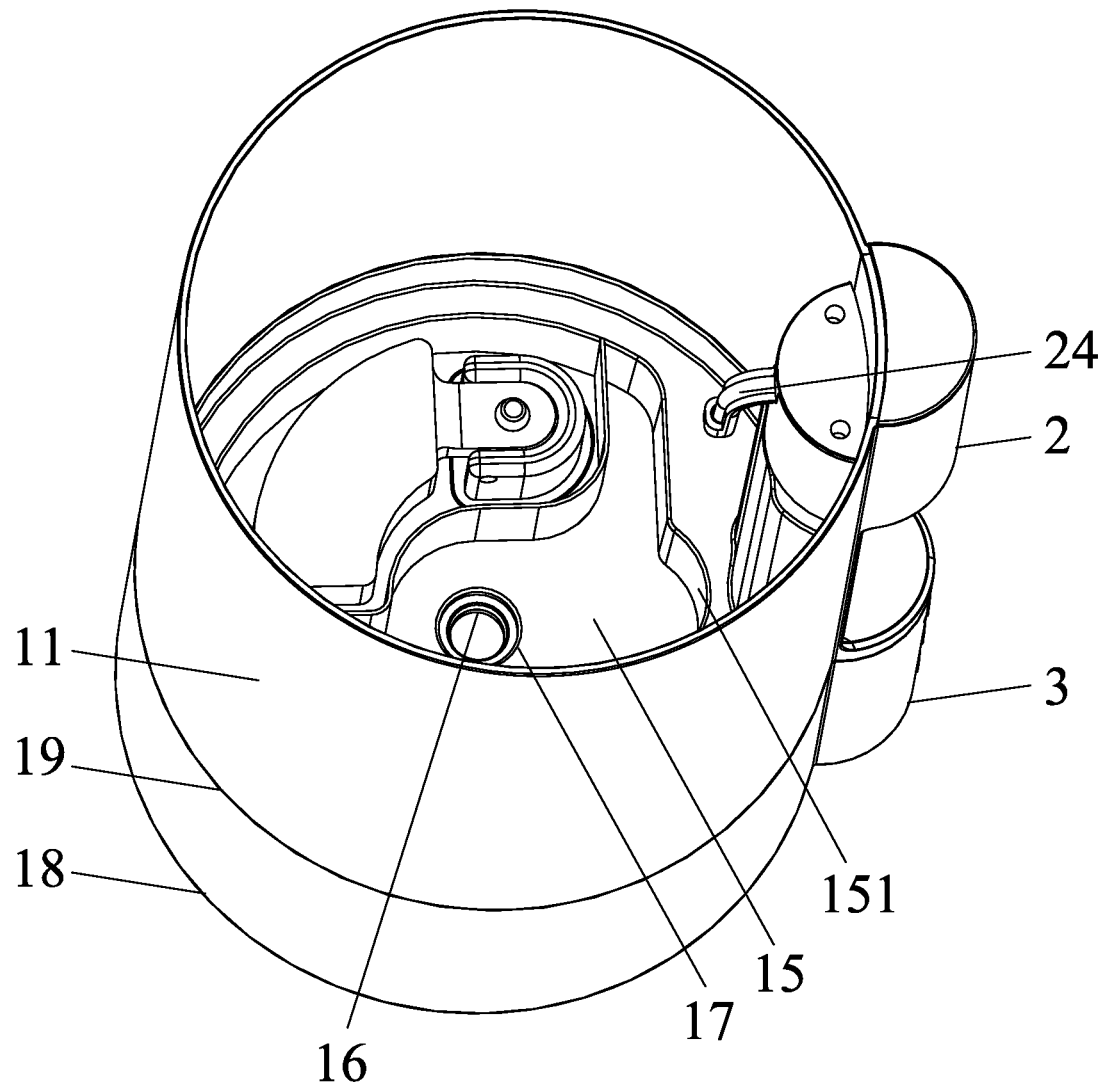
FIG. 3 is a perspective view of a first housing according to one embodiment of the disclosure.

In the example, the fixing member 24 comprises a hollow channel and at least part of the essential oil tube 25 is disposed in the hollow channel (as shown in FIG. 3). The humidifier further comprises a sidewall shared by the first housing and the second housing. The sidewall comprises a mounting hole; the fixing member 24 further comprises an arc-shaped end disposed through the mounting hole and extending into the first housing 21. The water passage 15 comprises an arc-shaped part 151 (as shown in FIG. 3). The essential oil flows out of the arc-shaped end and drips onto the arc-shaped part 151. When the fixing member 24 is disposed on the first container 12 and the essential oil is directly added to the first container 12, the concentration of the essential oil varies with amount of the water in the first container 12. For example, the addition of the essential oil increases the concentration of the essential oil in the water, and relatively large quantities of water leads to a low concentration of the essential oil. In this way, it is difficult to maintain a constant concentration of the essential oil in the water. In the example of the disclosure, the essential oil is added to the water passage 15 without disposing the fixing member 24 on the first container 12; and the water level in the water passage 15 remains unchanged, which is conducive to maintaining a constant concentration of the essential oil in the water.

Figure 4:
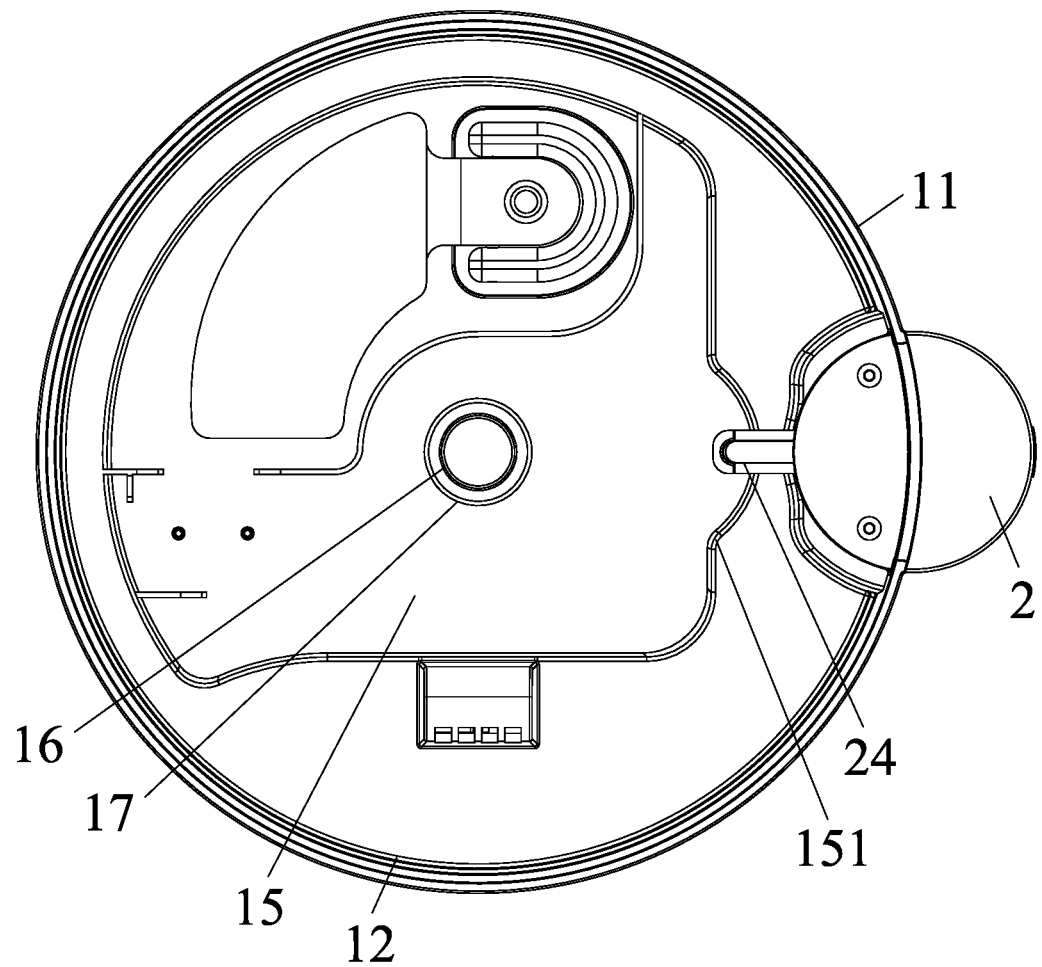
FIG. 4 is a top view of a first housing according to one embodiment of the disclosure.

Referring to FIGS. 3 and 4, the first housing 11 comprises a side wall, a partition 19, and a bottom plate 18. The control unit 3 comprises a plurality of lead wires or control wires. The partition 19 is disposed above the bottom plate 18. The partition 19 is connected to the side wall to form a first space for accommodation of the first container 12. A second space is defined by the bottom plate 18, the partition 19, and the side wall. The second space is disposed at the bottom of the first housing 11 and is configured to accommodate the ultrasonic atomizer 16, a power supply, and the plurality of lead wires (or control wires).

Referring to FIGS. 3 and 4, the water passage 15 is disposed below the partition and is configured to store the water flowing out of the first container 12. The water passage 15 comprises an atomization part 17 disposed on a central axis (i.e. a middle or central part) of the first housing 11. The water flows through the atomization part 17 and is atomized by the ultrasonic atomizer to produce mist. In the example, the ultrasonic atomizer 16 is disposed in the second space; and the water in the water passage 15 flows through the atomization part 17 into the ultrasonic atomizer 16 and is atomized to produce mist. In the example, a certain amount of water in the first container 12 flows through the water passage 15 per unit time; a certain amount of the essential oil is dripped onto the water passage 15, dispersed in the water, and atomized to humidify the air and produce the fragrant scent.

Figure 5:
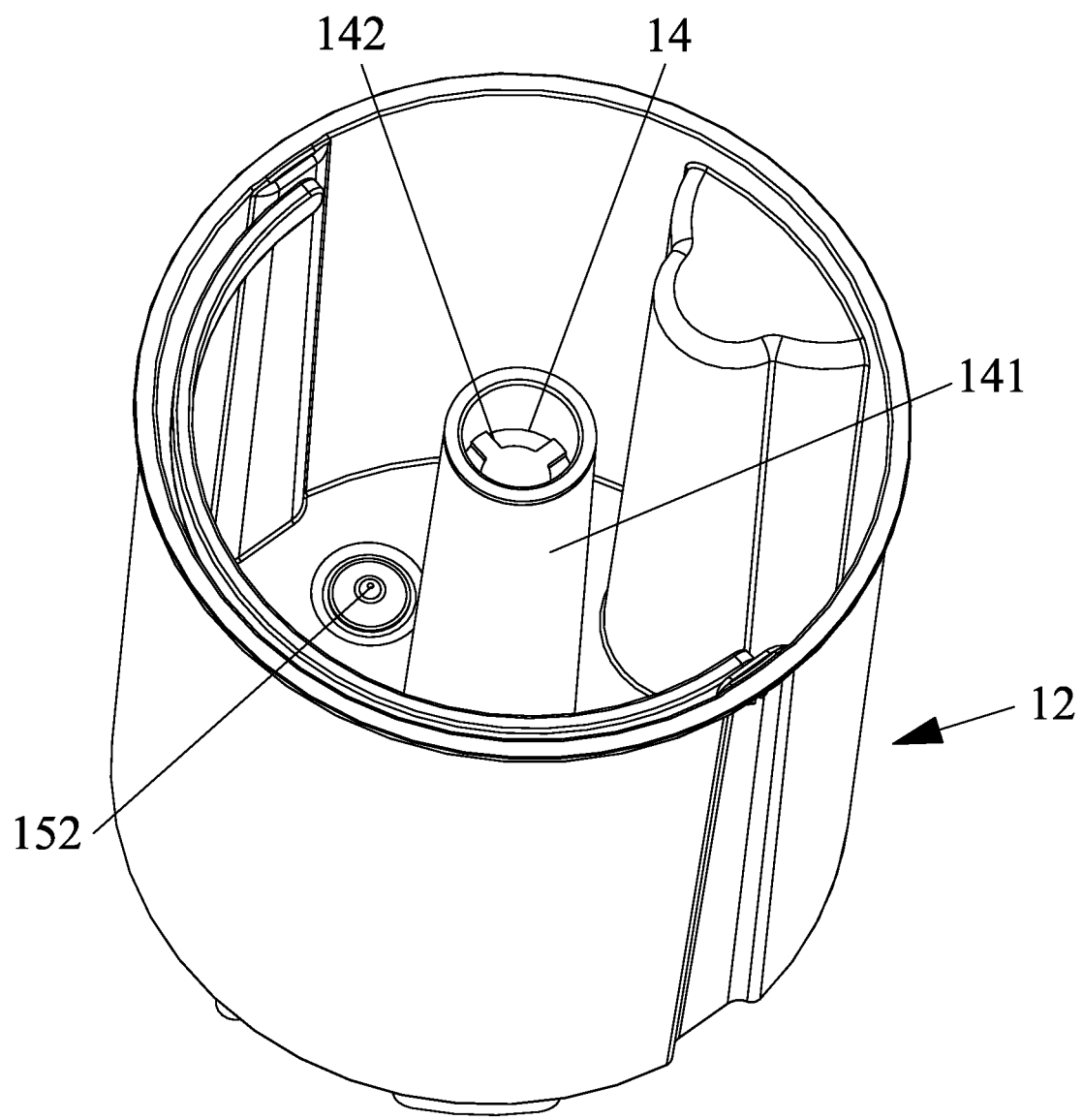
FIG. 5 is a perspective view of a first container according to one embodiment of the disclosure.
Figure 6:
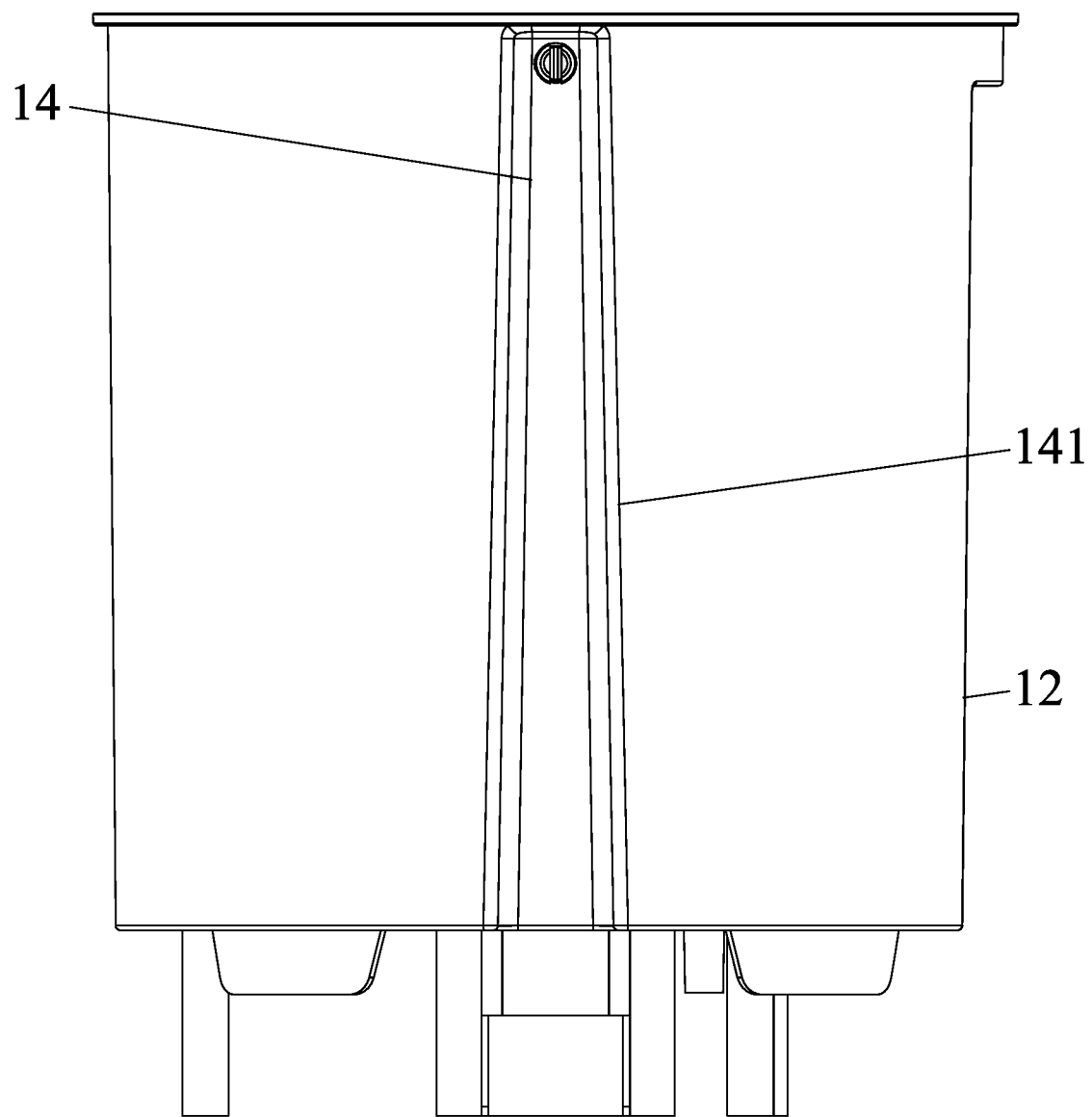
FIG. 6 is a cross-section view of a first container according to one embodiment of the disclosure.

Referring to FIGS. 5 and 6, the first container 12 is a hollow cylinder comprising a bottom surface and a side surface. The hollow cylinder comprises an overflow channel 14 and an open top. The overflow channel 14 is disposed along a central axis of the hollow cylinder and is disposed through the bottom surface to communicate with the water passage 15. The overflow channel 14 is configured to allow the mist from the ultrasonic atomizer 16 to the outside of the humidifier. The overflow channel 14 comprises a lateral surface 141 and is in the shape of a cylinder, a cone, or a truncated cone. A water container is defined by the bottom surface, the side surface, and the lateral surface 141 and is configured to store the water. The overflow channel 14 is disposed above the atomization part 17. The overflow channel 14 and the water container are separated by the lateral surface 141. Referring to FIG. 5, the humidifier further comprises a filter 142 disposed in the overflow channel 14, thus contributing to a slow and uniform release of the mist to emit.

In the example, the first container 12 further comprises a water outlet 152 disposed on the bottom surface and is configured to allow the water from the first container 12 to the water passage 15. The water outlet 152 is disposed above the water passage 15. The humidifier further comprises a water flow control module disposed at the water outlet 152. The water flow control module is configured to allow passage of water in the first container 12. The water flow control module is mechanically or electrically controlled so as to be turned on or off. In the example, the water outlet 152 is opened (to allow the water from the first container to the water passage 15) or closed (to prevent the passage of the water from the first container to the water passage 15) by a buoy valve or a solenoid valve. The buoy valve is disposed in the water passage 15 and comprises a float. When the water level in the water passage 15 rises, the float rises with the water level; once the float rises to a preset level, the buoy valve interrupts the water outlet 152. When the buoy valve is replaced with the solenoid valve, the control unit 3 is configured to direct the operation of the solenoid valve.

In the example, the humidifier further comprises a third housing 31 and the control unit 3 is disposed in the third housing 31. The control unit 3 is configured to control a working time and/or working state of the water atomization module 1, the essential oil delivery module 2, and the solenoid valve. The third housing 31 is fixedly embedded in a lower part of the recess 5. In the example, the control unit 3 comprises a circuit board disposed in the third housing 31. The circuit board comprises a control button and a control circuit. Output terminals of the control circuit are connected through wires to the components, such as peristaltic pump 23, the ultrasonic atomizer 16, and the solenoid valve, thus powering the components and sending control signals to the components. The components are independent of each other, so each of the components can be powered by a corresponding wire. The control circuit is configured to control the working time or working state of the components, thus adjusting the duration of the atomization, the amount of the essential oil, and the operation of the solenoid valve. In the example, the control button is configured to control the working state of the components, thus regulating the atomization process. The control unit 3 is disposed in the bottom portion of the humidifier to lower center of gravity. If there is a small amount of water left in the first container 12, even the control button is pressed, the humidifier is not easy to move due to the low center of gravity thereof.

It will be obvious to those skilled in the art that changes and modifications may be made, and therefore, the aim in the appended claims is to cover all such changes and modifications.

What is claimed is:

1. A device, comprising:
   a first housing, the first housing comprising an outer wall, and the outer wall comprising a recess;
   a second housing fixedly embedded in an upper part of the recess;
   a sidewall shared by the first housing and the second housing; the sidewall comprising a mounting hole;
   a first assembly comprising a first container, a water passage, and an ultrasonic atomizer;
   a second assembly comprising a head, an essential oil tube, an arc-shaped end having a hollow channel, and a peristaltic pump; and
   an essential oil container;
   wherein:
   the first assembly is disposed in the first housing;
   the second assembly is disposed in the second housing;
   the ultrasonic atomizer is configured to atomize water flowing out of the first container and entering the water passage into mist;
   the essential oil container is connected to the head of the second assembly; the essential oil tube and the peristaltic pump of the second assembly are configured to transfer essential oil from the essential oil container to the water passage so that the essential oil and the water are atomized together in the water passage;
   the essential oil tube is disposed through the head into the essential oil container; the essential oil tube comprises an essential oil discharge section and the arc-shaped end is configured to fix the essential oil discharge section; the peristaltic pump is configured to expel the air out of the essential oil tube so that the essential oil moves in the essential oil tube;
   the second housing comprises a bottom wall comprising a through hole; the head is disposed on the bottom wall of the second housing; the essential oil container is disposed through the through hole to connect to the head; the peristaltic pump is fixedly disposed in the second housing and above the head; the essential oil tube comprises a flexible tube; one end of the essential oil tube is disposed through the head into the essential oil container; the other end of the essential oil tube is fixed in the first housing by the arc-shaped end; the peristaltic pump comprises a rotating part; a middle part of the essential oil tube is disposed through the rotating part and the flexible tube is clamped or released as the rotating part rotates;

at least part of the essential oil tube is disposed in the hollow channel; the arc-shaped end is disposed through the mounting hole and extending into the first housing; the essential oil flows out of the arc-shaped end and drips into a set position of the first housing.

2. The device of claim 1, wherein the first housing comprises a side wall, a partition, and a bottom plate; the partition is disposed above the bottom plate; the partition is connected to the side wall to form a first space for accommodation of the first container; and a second space is defined by the bottom plate, the partition, and the side wall.

3. The device of claim 2, wherein the water passage is disposed below the partition and is configured to store the water flowing out of the first container; the water passage comprises an atomization part disposed on a central axis of the first housing; and the water flows through the atomization part and is atomized to produce mist.

4. The device of claim 3, wherein the ultrasonic atomizer is disposed in the second space; the water in the water passage flows through the atomization part and is atomized by the ultrasonic atomizer to produce the mist.

5. The device of claim 4, wherein the first container is a hollow cylinder comprising a bottom surface and a side surface; the hollow cylinder further comprises an overflow channel and an open top communicating with the overflow channel; the overflow channel is disposed along a central axis of the hollow cylinder, is disposed through the bottom surface and communicates with the water passage; the overflow channel is configured to allow the mist from the ultrasonic atomizer to flow out of the humidifier; the overflow channel comprises a lateral surface and is in the shape of a cylinder, a cone, or a truncated cone; a water container is defined by the bottom surface, the side surface, and the lateral surface and is configured to store the water; and a vertical projection of the overflow channel on the bottom surface is coincident with the atomization part.

6. The device of claim 5, wherein the first container further comprises a water outlet disposed on the bottom surface and is configured to allow the water to flow from the first container to the water passage; the water outlet is disposed above the water passage; the humidifier further comprises a buoy valve or solenoid valve disposed at the water outlet; and the buoy valve is mechanically or the solenoid valve is electrically controlled to allow the water to flow from the first container to the water passage.

7. The device of claim 6, wherein the humidifier further comprises a third housing and a control unit is disposed in the third housing; the control unit is configured to control a working time and/or working state of the ultrasonic atomizer in the first assembly and the peristaltic pump in the second assembly; and the third housing is embedded in a lower part of the recess.

* * * * *